US010357151B2

(12) United States Patent
Lu et al.

(10) Patent No.: US 10,357,151 B2
(45) Date of Patent: Jul. 23, 2019

(54) METHOD OF IDENTIFYING AND EYE DISORDER OF AN OBSERVER AND APPARATUS FOR IMPLEMENTING THE SAME

(71) Applicants: OHIO STATE INNOVATION FOUNDATION, Columbus, OH (US); INSTITUTE OF PSYCHOLOGY, CHINESE ACADEMY OF SCIENCES, Beijing (CN); ADAPTIVE SENSORY TECHNOLOGY, Boston, MA (US); BEIJING JUEHUA MEDICAL TECHNOLOGY CO., LTD., Beijing (CN)

(72) Inventors: Zhong-Lin Lu, Dublin, OH (US); Chang-Bing Huang, Beijing (CN); Wuli Jia, Beijing (CN); Luis A. Lesmes, San Diego, CA (US); Jiawei Zhou, Beijing (CN)

(73) Assignees: OHIO STATE INNOVATION FOUNDATION, Columbus, OH (US); ADAPTIVE SENSORY TECHNOLOGY, Boston, MA (US); BEIJING JUEHUA MEDICAL TECHNOLOGY CO., LTD., Beijing (CN); INSTITUTE OF PSYCHOLOGY, CHINESE ACADEMY OF SCIENCES, Beijing (CN)

(*) Notice: Subject to any disclaimer, the term of this patent is extended or adjusted under 35 U.S.C. 154(b) by 247 days.

(21) Appl. No.: 15/308,422
(22) PCT Filed: Apr. 30, 2015
(86) PCT No.: PCT/US2015/028657
§ 371 (c)(1),
(2) Date: Nov. 2, 2016
(87) PCT Pub. No.: WO2015/168477
PCT Pub. Date: Nov. 5, 2015

(65) Prior Publication Data
US 2017/0055823 A1 Mar. 2, 2017

Related U.S. Application Data

(60) Provisional application No. 61/987,700, filed on May 2, 2014.

(51) Int. Cl.
*A61B 3/00* (2006.01)
*A61B 3/02* (2006.01)
(Continued)

(52) U.S. Cl.
CPC ............ *A61B 3/022* (2013.01); *A61B 3/0025* (2013.01); *A61B 3/0033* (2013.01);
(Continued)

(58) Field of Classification Search
CPC combination set(s) only.
See application file for complete search history.

(56) References Cited

U.S. PATENT DOCUMENTS 5,381,196 A * 1/1995 Luce ...................... A61B 3/022
351/232
6,007,203 A * 12/1999 Seguin .................... A61B 3/02
351/211
(Continued)

FOREIGN PATENT DOCUMENTS

WO WO03/092482 11/2003
WO WO2013/170091 11/2013

OTHER PUBLICATIONS

American Academy of Family Physicians (2007). "Information from your family doctor. Amblyopia ("lazy eye") in your child". American Family Physician 75 (3): 368. PMID 17304868.
(Continued)

*Primary Examiner* — Sean P Dougherty
(74) *Attorney, Agent, or Firm* — Michael Best & Friedrich LLP

(57) ABSTRACT

Systems and methods for using an interocular inhibition procedure (IIP) for discriminating between anisometropic amblyopia and myopia, two disorders commonly confused in visual examination without proper optical correction. Opaque and translucent patching are positioned over the
(Continued)

fellow (or untested) eye resulting in different contrast sensitivities in the amblyopic (or tested) eye. A pinhole aperture may be used for identifying amblyopia and myopia/hyperopia.

21 Claims, 12 Drawing Sheets

(51) Int. Cl.
A61B 3/08 (2006.01)
A61B 3/032 (2006.01)
(52) U.S. Cl.
CPC ............ *A61B 3/0041* (2013.01); *A61B 3/032* (2013.01); *A61B 3/08* (2013.01)

(56) References Cited

U.S. PATENT DOCUMENTS

| | | | |
|---|---|---|---|
| 7,938,538 B2 | 5/2011 | Lu et al. | |
| 8,066,372 B2 | 11/2011 | Cooperstock et al. | |
| 2002/0140902 A1 | 10/2002 | Guirao et al. | |
| 2003/0020873 A1* | 1/2003 | Fink | A61B 3/0058 351/200 |
| 2004/0125341 A1* | 7/2004 | Fink | A61B 3/0058 351/211 |
| 2005/0213038 A1* | 9/2005 | Wertheim | A61B 3/02 351/222 |
| 2007/0052927 A1 | 3/2007 | Noda et al. | |
| 2008/0137037 A1 | 6/2008 | Kratzer et al. | |
| 2009/0091706 A1* | 4/2009 | Derr | A61B 3/0091 351/205 |
| 2009/0316111 A1 | 12/2009 | Hunter et al. | |
| 2010/0201942 A1 | 8/2010 | Hess et al. | |
| 2010/0283969 A1* | 11/2010 | Cooperstock | A61B 3/022 351/201 |
| 2011/0063571 A1 | 3/2011 | Duffy | |
| 2011/0085140 A1* | 4/2011 | Brown | A61B 3/022 351/239 |

OTHER PUBLICATIONS

Atkinson, J., O. Braddick, B. Bobier, S. Anker, D. Ehrlich, J. King, P. Watson and A. Moore (1996). "Two infant vision screening programmes: prediction and prevention of strabismus and amblyopia from photo- and videorefractive screening." Eye 10(2): 189-198.
Baker, D. H., T. S. Meese and R. F. Hess (2008). "Contrast masking in strabismic amblyopia: attenuation, noise, interocular suppression and binocular summation." Vision Res 48(15): 1625-1640.
Black, J. M., B. Thompson, G. Maehara and R. F. Hess (2011). "A compact clinical instrument for quantifying suppression." Optometry & Vision Science 88(2): E334-E343.
Brainard, D. H. (1997). "The psychophysics toolbox." Spatial vision 10(4): 433-436.
Campbell, F. and D. Green (1965). "Optical and retinal factors affecting visual resolution." The Journal of Physiology 181(3): 576.
Carlton, J., J. Karnon, C. Czoski-Murray, K. Smith and J. Marr (2008). "The clinical effectiveness and cost-effectiveness of screening programmes for amblyopia and strabismus in children up to the age of 4-5 years: a systematic review and economic evaluation." Health Technology Assessment, vol. 12: No. 25.
Castanes, M. (2002). "Major review: The underutilization of vision screening (for amblyopia, optical anomalies and strabismus) among preschool age children." Binocular vision & strabismus quarterly 18(4): 217-232.
Chou, R., T. Dana and C. Bougatsos (2011). "Screening for visual impairment in children ages 1-5 years: update for the USPSTF." Pediatrics, 127(2):e442-e479.
Cobo-Lewis, A. B. (1996). An Adaptive Method for Estimating Multiple Parameters of a Psychometric Function. 29th Annual Meeting of the Society for Mathematical Psychology. Journal of Mathematical Psychology, 40,353-354.
Ding, J. and G. Sperling (2006). "A gain-control theory of binocular combination." Proc Natl Acad Sci U S A 103(4): 1141-1146.
Dorr, M., L. A. Lesmes, Z.-L. Lu and P. J. Bex (2013). "Rapid and reliable assessment of the contrast sensitivity function on an iPad." Investigative ophthalmology & visual science 54(12): 7266-7273.
Ehrlich, M. I., R. D. Reinecke and K. Simons (1983). "Preschool vision screening for amblyopia and strabismus. Programs, methods, guidelines, 1983." Survey of ophthalmology 28(3): 145-163.
Eibschitz-Tsimhoni, M., T. Friedman, J. Naor, N. Eibschitz and Z. Friedman (2000). "Early screening for amblyogenic risk factors lowers the prevalence and severity of amblyopia." Journal of American Association for Pediatric Ophthalmology and Strabismus 4(4): 194-199.
Freeman, A. W. and N. Jolly (1994). "Visual loss during interocular suppression in normal and strabismic subjects." Vision research 34(15): 2043-2050.
Harrad, R. and R. Hess (1992). "Binocular integration of contrast information in amblyopia." Vision research 32(11): 2135-2150.
Harrad, R., F. Sengpiel and C. Blakemore (1996). "Physiology of suppression in strabismic amblyopia." British Journal of Ophthalmology 80(4): 373-377.
Hess, R. F., Y.-Z. Wang, R. Demanins, F. Wilkinson and H. R. Wilson (1999). "A deficit in strabismic amblyopia for global shape detection." Vision research 39(5): 901-914.
Holmes, J. M. and M. P. Clarke (2006). "Amblyopia." The Lancet 367(9519): 1343-1351.
Hou, F., C. B. Huang, L. Lesmes, L. X. Feng, L. Tao, Y. F. Zhou and Z. L. Lu (2010). "qCSF in clinical application: efficient characterization and classification of contrast sensitivity functions in amblyopia." Invest Ophthalmol Vis Sci 51(10): 5365-5377.
Huang, C.-B., J. Zhou, Y. Zhou and Z.-L. Lu (2010). "Contrast and Phase Combination in Binocular Vision." PLoS ONE vol. 5(Issue 12).
Huang, C.-B., J. Zhou, Z.-L. Lu and Y. Zhou (2011). "Deficient binocular combination reveals mechanisms of anisometropic amblyopia: Signal attenuation and interocular inhibition." Journal of vision 11(6): 4, 1-17.
Huang, P. C., D. H. Baker and R. F. Hess (2012). "Interocular suppression in normal and amblyopic vision: spatio-temporal properties." J Vis 12(11):29, 1-12.
Hunter, D. G., D. S. Nassif, R. Winsor, B. I. Gramatikov, D. L. Guyton and N. V. Piskun (2004). "Pediatric Vision Screener 1: instrument design and operation." Journal of biomedical optics 9(6): 1363-1368.
Ingram, R. (1977). "Refraction as a basis for screening children for squint and amblyopia." British Journal of Ophthalmology 61(1): 8-15.
Kim, W., M. A. Pitt, Z.-L. Lu, M. Steyvers and J. I. Myung (2013). "A Hierarchical Adaptive Approach to Optimal Experimental Design." King-Smith, P. E., S. S. Grigsby, A. J. Vingrys, S. C. Benes and A. Supowit (1994). "Efficient and unbiased modifications of the QUEST threshold method: theory, simulations, experimental evaluation and practical implementation." Vision Res 34(7): 885-912.
Kiorpes, L., C. Tang and J. A. Movshon (1999). "Factors limiting contrast sensitivity in experimentally amblyopic macaque monkeys." Vision research 39(25): 4152-4160.
Kontsevich, L. L. and C. W. Tyler (1999). "Bayesian adaptive estimation of psychometric slope and threshold." Vision Res 39(16): 2729-2737.
Kujala, J. V. and T. J. Lukka (2006). "Bayesian adaptive estimation: The next dimension." Journal of Mathematical Psychology 50(4): 369-389.
Lai, X. J., J. Alexander, M. G. He, Z. K. Yang and C. Suttle (2012). "A novel apparatus for interocular interaction evaluation in children with and without anisometropic amblyopia." Clin Exp Optom 95(4): 410-420.
Lai, X. J., J. Alexander, M. He, Z. Yang and C. Suttle (2011). "Visual functions and interocular interactions in anisometropic children with and without amblyopia." Investigative ophthalmology & visual science 52(9): 6849-6859.

(56) References Cited

OTHER PUBLICATIONS

Lesmes, L. A., L. Z-L, B. J and A. T. "Efficient Adaptive Estimation of the Contrast Sensitivity Function: the qCSF method." J Vis. 2010, 10(3): 17.1-1721.
Lesmes, L. A., S. T. Jeon, Z. L. Lu and B. A. Dosher (2006). "Bayesian adaptive estimation of threshold versus contrast external noise functions: the quick TvC method." Vision Res 46(19): 3160-3176.
Lesmes, L. A., Z.-L. Lu, J. Baek and T. D. Albright (2010). "Bayesian adaptive estimation of the contrast sensitivity function: The quick CSF method." Journal of Vision 10(3):17, 1-21.
Levi, D. M. and S. Klein (1982). "Differences in vernier discrimination for grating between strabismic and anisometropic amblyopes." Investigative Ophthalmology & Visual Science 23(3): 398-407.
Li, J., B. Thompson, C. S. Lam, D. Deng, L. Y. Chan, G. Maehara, G. C. Woo, M. Yu and R. F. Hess (2011). "The role of suppression in amblyopia." Invest Ophthalmol Vis Sci 52(7): 4169-4176.
Li, X., Z.-L. Lu, P. Xu, J. Jin and Y. Zhou (2003). "Generating high gray-level resolution monochrome displays with conventional computer graphics cards and color monitors." Journal of neuroscience methods 130(1): 9-18.
Loudon, S. E., C. A. Rook, D. S. Nassif, N. V. Piskun and D. G. Hunter (2011). "Rapid, high-accuracy detection of strabismus and amblyopia using the pediatric vision scanner." Investigative ophthalmology & visual science 52(8): 5043-5048.
Mou, T. (1966). "Logarithmic visual acuity chart and five-score recording." Chinese Journal of Ophthalmology 13(1): 96-106.
Mower, G. D., W. G. Christen, J. L. Burchfiel and F. H. Duffy (1984). "Microiontophoretic bicuculline restores binocular responses to visual cortical neurons in strabismic cats." Brain research 309(1): 168-172.
Naidoo, K., Kovin, P. (2002). "Case Finding in the Clinic: Refractive Errors". J Comm Eye Health 15 (43): 39-40.
Narasimhan, S., E. R. Harrison and D. E. Giaschi (2012). "Quantitative measurement of interocular suppression in children with amblyopia." Vision research 66: 1-10.
Pelli, D. G. (1997). "The VideoToolbox software for visual psychophysics: Transforming numbers into movies." Spatial vision 10(4): 437-442.
Regan, D., J. Raymond, A. Ginsburg and T. Murray (1981). "Contrast sensitivity, visual acuity and the discrimination of Snellen letters in multiple sclerosis." Brain 104(2): 333-350.
Reynaud, A., Y. Tang, Y. Zhou and R. F. Hess (2014). "A normative framework for the study of second-order sensitivity in vision." Journal of vision 14(9): 3, 1-16.
Rosén, R., L. Lundström, A. P. Venkataraman, S. Winter and P. Unsbo (2014). "Quick contrast sensitivity measurements in the periphery." Journal of vision 14(8): 3, 1-10.
Schmidt, P., M. Maguire, V. Dobson, G. Quinn, E. Ciner, L. Cyert, M. T. Kulp, B. Moore, D. Orel-Bixler and M. Redford (2004). "Comparison of preschool vision screening tests as administered by licensed eye care professionals in the Vision In Preschoolers Study." Ophthalmology 111(4): 637-650.
Sengpiel, F., K.-U. Jirmann, V. Vorobyov and U. T. Eysel (2006). "Strabismic suppression is mediated by inhibitory interactions in the primary visual cortex." Cerebral Cortex 16(12): 1750-1758.
Simons, K. (2005). "Amblyopia characterization, treatment, and prophylaxis." Sury Ophthalmol 50(2): 123-166.
Sireteanu, R., M. Fronius and W. Singer (1981). "Binocular interaction in the peripheral visual field of humans with strabismic and anisometropic amblyopia." Vision research 21(7): 1065-1074.
Sjöstrand, J. and M. Abrahamsson (1996). "Prevention of amblyopia and the concept of cure." European journal of ophthalmology 7(2): 121-129.
Song, S., D. M. Levi and D. G. Pelli (2014). "A double dissociation of the acuity and crowding limits to letter identification, and the promise of improved visual screening." Journal of Vision 14(5): 3, 1-37.
van Gaalen, K. W., N. M. Jansonius, S. A. Koopmans, T. Terwee and A. C. Kooijman (2009). "Relationship between contrast sensitivity and spherical aberration: comparison of 7 contrast sensitivity tests with natural and artificial pupils in healthy eyes." Journal of Cataract & Refractive Surgery 35(1): 47-56.
Wall, T. C., W. Marsh-Tootle, H. H. Evans, C. A. Fargason Jr, C. S. Ashworth and J. M. Hardin (2002). "Compliance with vision-screening guidelines among a national sample of pediatricians." Ambulatory Pediatrics 2(6): 449-455.
Watson, A. B. and A. J. Ahumada (2005). "A standard model for foveal detection of spatial contrast." Journal of Vision 5(9): 717-740.
Watson, A. B. and D. G. Pelli (1983). "QUEST: A Bayesian adaptive psychometric method." Percept Psychophys 33(2): 113-120.
Wildsoet, C., J. Wood, H. Maag and S. Sabdia (1998). "The effect of different forms of monocular occlusion on measures of central visual function." Ophthalmic and Physiological Optics 18(3): 263-268.
Wu, C. and D. G. Hunter (2006). "Amblyopia: diagnostic and therapeutic options." American journal of ophthalmology 141(1): 175-184. e172.
Yang, J. and S. B. Stevenson (1999). "Post-retinal processing of background luminance." Vision research 39(24): 4045-4051.
Ying GS, Kulp MT, Maguire M, et al., "Sensitivity of screening tests for detecting Vision in Preschoolers-targeted vision disorders when specificity is 94%," Optom Vis Sci 2005; 82(5):432-438.
Zhou, J., P. C. Huang and R. F. Hess (2013). "Interocular suppression in amblyopia for global orientation processing." J Vis 13(5): 19, 1-14.
Zhou, J., S. McNeal, R. J. Babu, D. H. Baker, W. R. Bobier and R. F. Hess (2014). "Time course of dichoptic masking in normals and suppression in amblyopes." Invest Ophthalmol Vis Sci 55(7): 4098-4104.
Zhou, Y., C. Huang, P. Xu, L. Tao, Z. Qiu, X. Li and Z. L. Lu (2006). "Perceptual learning improves contrast sensitivity and visual acuity in adults with anisometropic amblyopia." Vision Res 46(5): 739-750.
International Search Report and Written Opinion for Application No. PCT/US2015/028657 dated Jul. 29, 2015 (13 pages).
Hess et al., "Binocular vision in amblyopia: structure, suppression and plasticity," Ophthalmic and Physiological Optics, 2014, vol. 34, No. 2, pp. 146-162.
European Patent Office Extended Search Report for Application No. 15786707.8 dated Jan. 8, 2018 (8 pages).

* cited by examiner

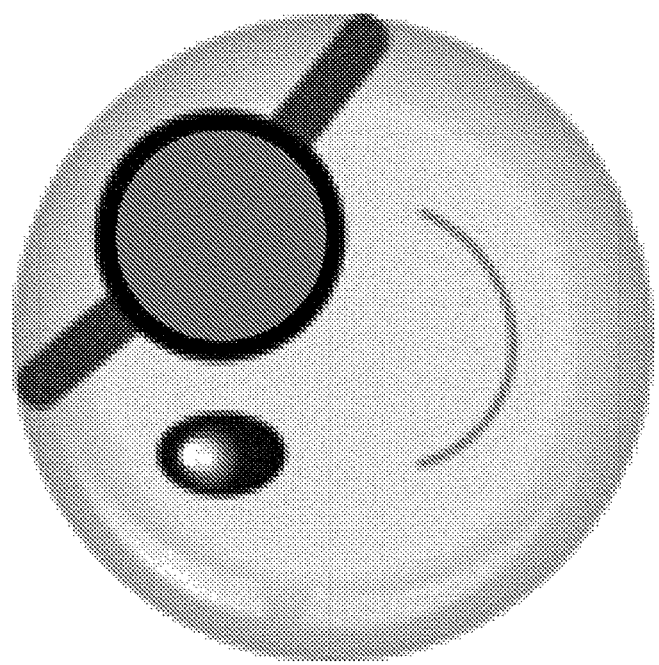
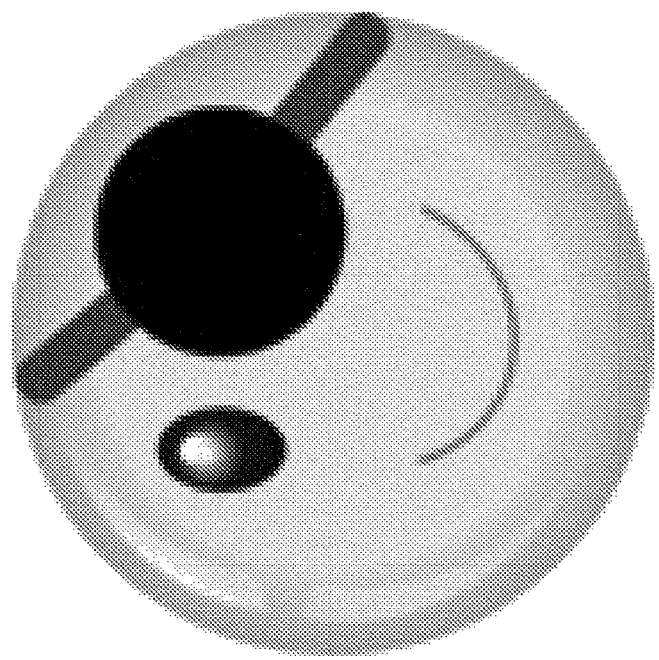
Fig 1

Table 1. Characteristics of amblyopic observers

| No. | Sex | Age(y) | AE Correction | AE Acuity(LogMAR)* | FE Correction | FE Acuity(LogMAR)* |
|---|---|---|---|---|---|---|
| 1 | F | 24 | +0.50DS:+0.25DC×45 | 0.58/0.57 | -9.00DS | 0.66/0.09 |
| 2 | F | 6 | +2.50DS:+1.50DC×80 | 0.34/0.29 | +2.00DS:+0.50DC×83 | 0.18/0.07 |
| 3 | F | 32 | +2.50DS:+1.50DC×30 | Null/0.76 | +0.50DS | Null/-0.02 |
| 4 | F | 18 | -1.00DS:+1.25DC×107 | 0.28/0.28 | -2.75DS:-0.75×158 | 0.68/-0.02 |
| 5 | F | 26 | +3.50DS | 0.58/0.38 | -3.00DS | 0.27/-0.07 |
| 6 | M | 28 | +4.5DS | 0.58/0.48 | -2.75DS | 0.57/0.07 |
| 7 | F | 25 | +2.75DS | 0.07/0.07 | Plano | 0.06/0.06 |
| 8 | M | 31 | +1.00DS:+0.50DC×90 | 0.63/0.55 | -3.5DS:+0.50DC×10 | 0.36/-0.02 |
| 9 | F | 24 | +1.23DS:+1.25DC×90 | 0.38/0.25 | Plano | -0.13/-0.13 |
| 10 | M | 24 | +2.75DS:+1.50DC×105 | 0.73/0.48 | Plano | -0.02/-0.02 |
| 11 | M | 8 | +0.75DS:+1.50DC×70 | Null/0.38 | +1.75DS | Null/-0.13 |
| 12 | M | 17 | +4.37DS:-3.12DC×23 | 0.68/0.73 | +0.87DS:-0.37DC×170 | -0.17/-0.20 |
| 13 | F | 23 | +0.25DS | Null/1.30 | +0.50DC×180 | Null/-0.02 |
| 14 | F | 20 | +5.00DS | 0.38/0.29 | +1.00DS | -0.10/-0.25 |
| 15 | F | 11 | +2.25DS:+1.00DC×78 | 1.10/1.10 | Plano | -0.02/-0.02 |
| 16 | F | 13 | +2.50DS:+1.00DC×115 | 0.18/0.09 | -1.00DS | 0.18/-0.02 |
| 17 | M | 12 | -5.25DS:-0.50DC×44 | 1.05/0.18 | -2.00DS:-0.75DC×7 | 0.45/0.00 |
| 18 | M | 9 | +3.00DS:-5.00DC×175 | 0.07/-0.02 | +1.50DS:-4.00DC×175 | 0.07/-0.02 |
| 19 | F | 23 | +2.00DS:+0.50DC×79 | 0.78/0.28 | Plano | -0.02/-0.02 |

*Acuities were arranged as 'Naked condition/Full corrected condition'.

*Fig. 2*

Table 2. Characteristics of myopic observers

| No. | Sex | Age(y) | OD Correction | OD Acuity(LogMAR)* | OS Correction | OS Acuity (LogMAR)* |
|---|---|---|---|---|---|---|
| 1 | F | 25 | -6.50DS | 0.58/-0.07 | -6.50DS | 0.48/-0.13 |
| 2 | M | 23 | -4.0DS | 0.85/0.00 | -3.0DS | 0.85/-0.02 |
| 3 | M | 27 | -6.0DS:-1.0DC×180 | 0.68/-0.10 | -7.5DS:-1.0DC×180 | 0.78/-0.02 |
| 4 | M | 22 | -3.50DS:-0.75DC×7 | 0.38/-0.03 | -3.50DS:-1.00DC×176 | 0.26/-0.13 |
| 5 | M | 26 | -6.0DS | 0.88/0.00 | -4.75DS | 0.88/-0.11 |
| 6 | M | 35 | -6.50DS | 0.58/-0.02 | -5.50DS | 0.48/-0.02 |
| 7 | M | 24 | -3.5DS | 0.48/-0.07 | -3.5DS | 0.40/-0.03 |
| 8 | M | 25 | -3.00DS | 0.66/-0.15 | -2.00DS:-5.0DC×165 | 0.58/-0.11 |
| 9 | M | 23 | -1.75DS | 0.57/-0.02 | -1.5DS | 0.48/0.00 |
| 10 | M | 25 | -5.50DS | 0.58/0.09 | -7.0DS | 0.58/0.07 |
| 11 | M | 32 | -4.50DS | 0.68/-0.05 | -4.50DS | 0.68/-0.03 |
| 12 | F | 29 | -1.75DS | -0.11/-0.11 | -1.75DS | -0.13/-0.14 |
| 13 | F | 24 | -2.75DS | 0.40/-0.20 | -2.75DS | 0.34/-0.23 |
| 14 | M | 27 | -8.00DS | 0.88/0.28 | -5.00DS | 0.68/0.28 |
| 15 | M | 25 | -3.00DS | 0.76/0.09 | -2.00DS | 0.40/-0.01 |
| 16 | M | 23 | -3.5DS | 0.88/0.07 | -3.0DS | 0.78/-0.02 |
| 17 | M | 24 | -4.0DS | 0.73/-0.10 | -3.0DS | 0.27/0.00 |
| 18 | F | 19 | -4.0DS | 0.57/0.06 | -3.0DS | 0.29/-0.07 |
| 19 | F | 23 | -3.0DS | 0.85/-0.07 | -2.0DS | 0.85/-0.10 |
| 20 | M | 22 | -3.0DS | 0.47/-0.11 | -5.0DS | 0.66/-0.11 |
| 21 | F | 22 | -5.0DS | 0.76/-0.03 | -5.0DS | 0.73/-0.04 |
| 22 | M | 21 | -4.25DS | 0.88/-0.04 | -4.0DS | 0.68/-0.04 |

*Acuities were arranged as 'Naked condition/Full corrected condition'.

Fig. 3

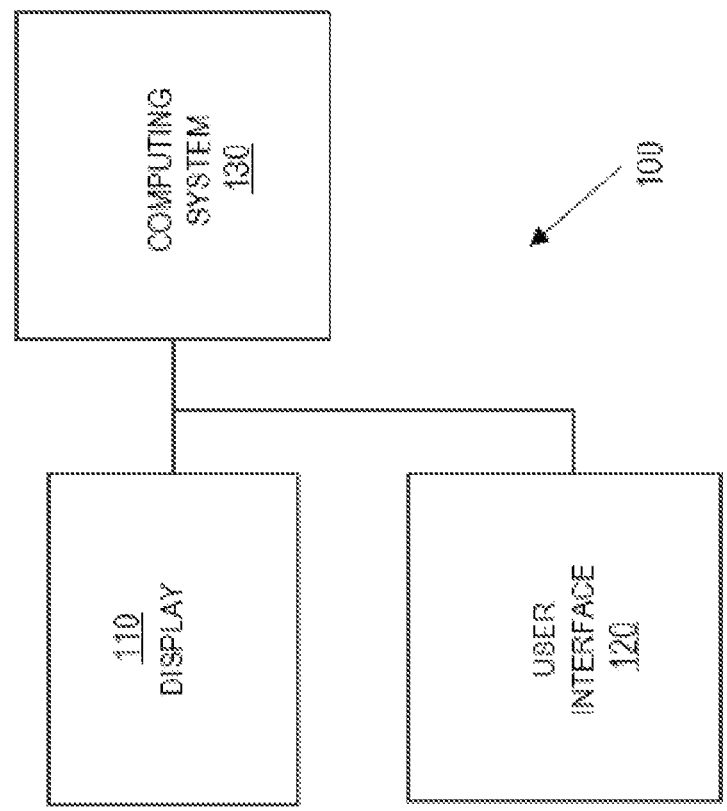
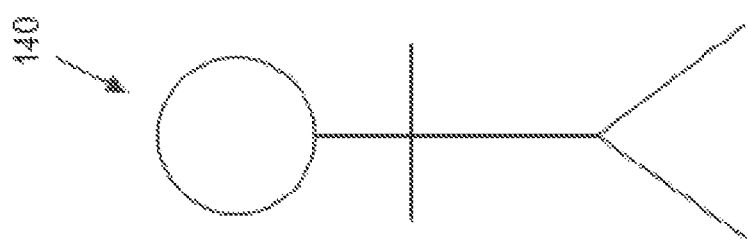
FIG. 5

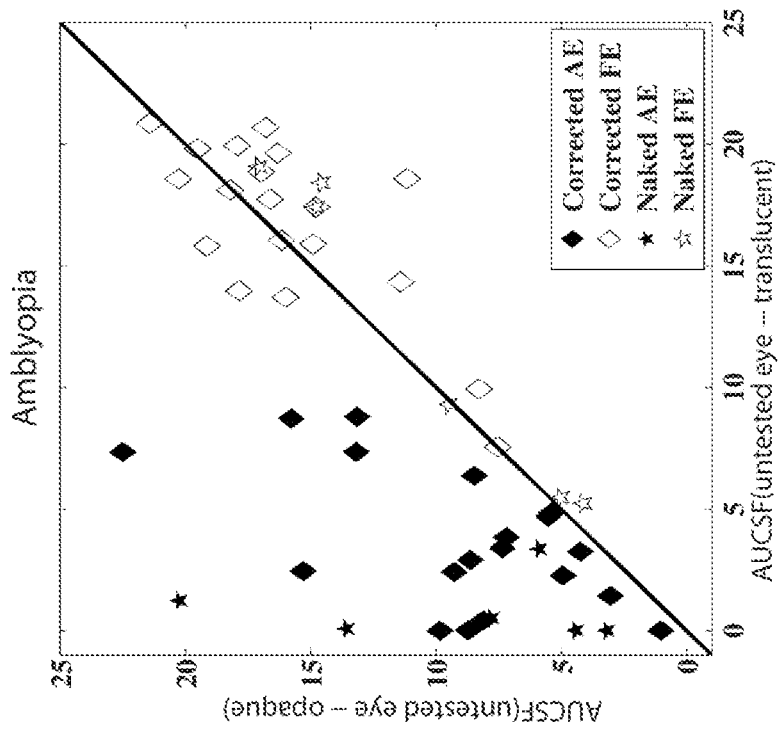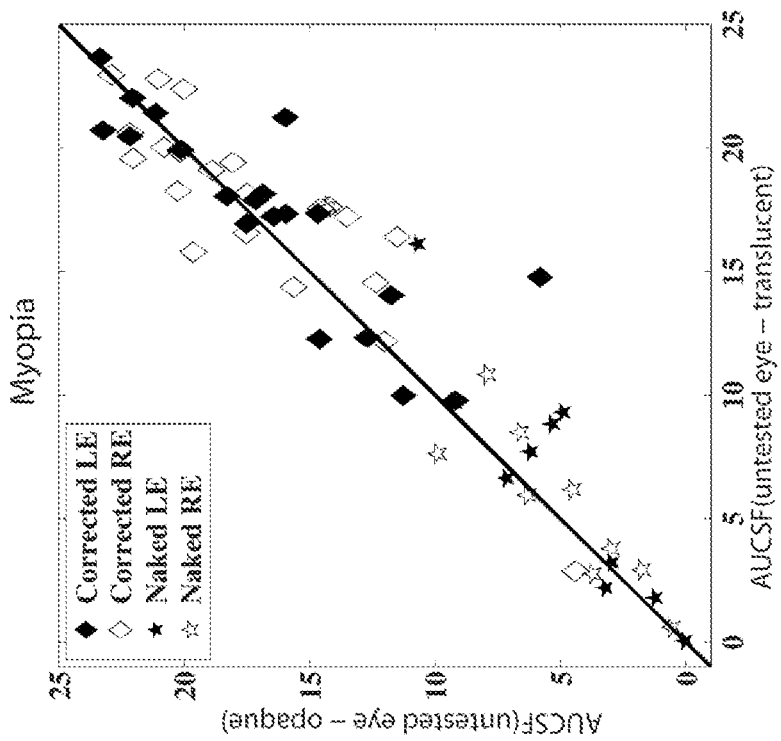
Fig. 8

Table 3. The power of single metrics and the best discriminator(s) in identifying amblyopia.

| Factors | Amblyopia Identifying (%) | |
|---|---|---|
| | Naked | Corrected |
| Interocular Visual Acuity Difference (IVAD) | Null | 95.1 |
| Interocular AUCSF Difference (Translucent) | Null | 82.9 |
| Interocular AUCSF Difference (Opaque) | Null | 75.6 |
| Interocular Cutoff Difference (Translucent) | Null | 65.9 |
| Interocular Cutoff Difference (Opaque) | Null | Null |
| Inhibition Index (I2) | 100 | 82.9 |
| Best Combination of Metric(s) | 100(I2) | 100(I2 and IVAD) |

Null: the particular predictor didn't significantly improve the discriminating power relative to the case without any predictors (with only the constant).

Fig. 9

Table 4. Characteristics of myopic participants

| No. | Sex | Age(y) | Eye | Correction | Naked Acuity (LogMAR) | Full Corrected Acuity(LogMAR) |
|---|---|---|---|---|---|---|
| 1 | F | 26 | OD | -6.50DS | 0.58 | -0.07 |
|   |   |    | OS | -6.50DS | 0.48 | -0.13 |
| 2 | M | 36 | OD | -6.50DS | 0.58 | -0.02 |
|   |   |    | OS | -5.50DS | 0.48 | -0.02 |
| 3 | M | 24 | OD | -1.50DS | 0.48 | -0.05 |
|   |   |    | OS | Plano | 0 | 0 |

*Fig. 10*

METHOD OF IDENTIFYING AND EYE DISORDER OF AN OBSERVER AND APPARATUS FOR IMPLEMENTING THE SAME

CROSS-REFERENCE TO RELATED APPLICATION(S)

This is a U.S. national stage entry of International Patent Application No. PCT/US2015/028657, filed on Apr. 30, 2015, which claims priority to U.S. Provisional Patent Application No. 61/987,700, filed on May 2, 2014, the entire contents of all of which are fully incorporated herein by reference.

BACKGROUND

The invention relates to methods of and apparatus for identifying an eye disorder of an observer. More specifically, the invention relates to identifying an eye disorder, such as amblyopia and myopia, by performing multiple contrast sensitivity function procedures and comparing the results of the procedures.

Early detection can be critical for successful treatment of amblyopia ("lazy eye"), the most common cause of monocular visual impairment in children and young adults that affects 2-5% of the population. Earlier detection of the disorder and correction of the underlying cause (strabismus, refractive error, and/or form deprivation) can provide better long-term treatment outcomes.

A typical amblyopia screening/diagnosis procedure includes assessments of visual acuity, stereo acuity, and presence of amblyopiogenic factors (e.g. strabismus and refractive errors). With no single agreed-upon criterion, one common metric for diagnosing amblyopia is the interocular difference in visual acuity, after exclusion of potential organic defects, refractive error, and strabismus. Recent studies have proposed other potential metrics for diagnosing amblyopia, including interocular differences in contrast sensitivity and in particular the difference in cutoff spatial frequencies. The Pediatric Vision Scanner (PVS), a portable device based on retinal birefringence scanning, has also been developed to automatically detect strabismus, amblyopia, and other serious eye conditions in children as young as 2 years of age. Studies evaluating candidate screening methods for amblyopia have concluded that although tests may differ in terms of screening sensitivity and specificity, the estimated likelihood of amblyopia occurrence was comparable among the tests, and combining different tests could improve diagnostic accuracy.

Although amblyopia screening can be performed in schools, by pediatricians or eye care specialists, automated photo-screening programs usually require specialized instruments and specific expertise. For example, the most common screening procedure assesses visual acuity differences in the potential amblyopic eye between conditions with and without (naked eye) refractive correction. The procedures mandate good compliance, proper eye alignment and refractive error measurements, and accurate prescription of eyeglasses. The screening process can be expensive and inefficient, and is not always easily accessible. There remains an important need for efficient, easy-to-perform, affordable, and reliable screening methods.

SUMMARY

In one embodiment, the invention provides the use of an interocular inhibition procedure (IIP) for discriminating between anisometropic amblyopia and myopia, two disorders commonly confused in visual examination without proper optical correction. Using the binocular combination paradigm, the inventors have demonstrated that deficient binocular vision in anisometropic amblyopia results from a combination of monocular signal attenuation in the amblyopic eye and stronger inhibition from the fellow eye to the amblyopic eye. The IIP is based on the observation of the stronger inhibition from the fellow eye to the amblyopic eye in anisometropic amblyopia and the approximately balanced inhibition between the eyes in normal and myopic vision. For patients with amblyopia, the inventors identified that opaque and translucent patching over the fellow (or untested) eye would result in different contrast sensitivities in the amblyopic eye, while different patching over the amblyopic eye would not change the contrast sensitivities of the fellow eye. For normal and myopic subjects, patching with opaque and translucent media over one eye would not significantly change the contrast sensitivities of the other eye. Specifically, for amblyopes, patching the fellow eye with an opaque medium will lead to better function in the amblyopic eye compared to patching the fellow eye with a translucent medium because patching with an opaque medium can better release the amblyopic eye from inhibition exerted by the fellow eye.

In at least one implementation, the invention compared contrast sensitivity of the tested eye when the untested eye was patched either with an opaque or a translucent medium. In at least one implementation, the comparison included the adaptive assessment of full contrast sensitivity functions (CSF), instead of assessment of contrast sensitivity at a single frequency. A Bayesian adaptive procedure was used to efficiently measure the CSF in the tested eye while the untested eye was covered with opaque or translucent patching. For the tested eye, the area under CSF (AUCSF), also sometimes calculated as area under log CSF (AULCSF) and cutoff spatial frequencies were obtained for both translucent and opaque patching conditions, and an inhibition index was calculated as the AUCSF ratio between the two patching conditions. The same procedure was repeated as the patching was switched between the previously tested and untested eyes. The changing of the patching of the fellow eye drastically changed the CSFs in the amblyopic eye. The same manipulation had no significant impact on the CSFs of the fellow eyes of amblyopic subjects, nor on the CSFs of both eyes of the myopic subjects. The effect provides a simple and efficient method to discriminate anisometropic amblyopia from uncorrected myopia. The IIP may be used for early amblyopia screening.

In one embodiment, the invention provides a use of CSFs obtained through a pinhole aperture in front of the tested eye to discriminate amblyopia from myopia or hyperopia. Whereas myopia/hyperopia is an optical problem, amblyopia is a cortical disorder that cannot be corrected through optical correction. The method measures CSF of the tested eye either directly or through a pinhole aperture while the untested eye is patched with an opaque medium. The pinhole aperture is used to bypass optical limitations in myopia/hyperopia, but it can't correct the cortical problems in amblyopia. For a myopic/hyperopic eye, a pinhole aperture can be used to reduce effects of defective optics and improve contrast sensitivity, but a pinhole aperture provides the amblyopic eye with less relative improvement. Comparison of the effects on the CSF provided by a pinhole aperture allows one to distinguish amblyopic vision from myopic/hyperopic vision.

In one embodiment, CSFs collected with and without a pinhole aperture are compared. For subjects with myopia or hyperopia, AUCSFs of both eyes are improved in the pinhole condition. But, for patients with amblyopia, AUCSF of the amblyopic eye does not significantly change or changes much less in the two conditions.

In another embodiment, the invention provides a method of identifying an eye disorder of an observer. The method is accomplished with an apparatus having a display, a user interface, and a processor. The method includes the display generating first stimuli for the observer while an untested eye of the observer is covered with a translucent medium, and the display generating second stimuli for the observer while the untested eye of the observer is covered with an at least substantially opaque medium. The first stimuli are generated as part of a first trial for a tested eye of the observer, and the second stimuli are generated as part of a second trial for the tested eye. The method further includes the user interface receiving first input during the first trial and second input during the second trial; the processor determining a first contrast sensitivity function (CSF) using the first input and a second contrast sensitivity function (CSF) using the second input, the processor calculating a first area under contrast sensitivity function (AUCSF) for the first CSF and a second area under contrast sensitivity function (AUCSF) for the second CSF. The method also includes the processor defining an inhibition index for the first and second trials as the ratio of one of the first AUCSF and the second AUCSF over the other of the first AUCSF and the second AUCSF, and the processor identifying an eye disorder (e.g., amblyopia) for the tested eye of the observer using the inhibition index.

In another embodiment, the invention provides a method of identifying an eye disorder of an observer. The method is accomplished with an apparatus having a display, a user interface, and a processor. The method includes the display generating first stimuli for the observer while an untested eye of the observer is covered with an at least substantially opaque medium and a tested eye of the observer is substantially uncovered, and the display generating second stimuli for the observer while the untested eye of the observer is covered with the at least substantially opaque medium and the tested eye views the display through a pinhole aperture. The first stimuli are generated as part of a first trial for the tested eye, and the second stimuli are generated as part of a second trial for the tested eye. The method further includes the user interface receiving first input during the first trial and second input during the second trial; the processor determining a first contrast sensitivity function (CSF) using the first input and a second contrast sensitivity function (CSF) using the second input, the processor calculating a first area under contrast sensitivity function (AUCSF) for the first CSF and a second area under contrast sensitivity function (AUCSF) for the second CSF. The method also includes the processor defining an optical factor for the first and second trials as the ratio of one of the first AUCSF and the second AUCSF over the other of the first AUCSF and the second AUCSF, and the processor identifying an eye disorder (e.g., myopia) for the tested eye of the observer using the optical factor.

In another embodiment, the invention provides an apparatus for determining an eye disorder for an observer having a tested eye and an untested eye. The apparatus can be an electronic device or a computer system. The apparatus includes a display, a user interface, a processor, and a non-transitory medium comprising instructions. The processor can execute the instructions to perform the method of determining an eye disorder (e.g., amblyopia) for the observer.

Other aspects of the invention will become apparent by consideration of the detailed description and accompanying drawings.

BRIEF DESCRIPTION OF THE DRAWINGS

FIG. 1 is an illustration of the interocular inhibition procedure (IIP) with the untested eye patched with opaque (a) and translucent (b) media.

FIG. 2 is a table providing characteristics of amblyopic observers.

FIG. 3 is a table providing characteristics of myopic observers.

FIG. 5 is a block diagram illustrating components of a system for implementing the quick CSF procedure and identifying an eye disorder of an observer.

FIG. 8 are graphs representing AUCSF for myopic (left) and amblyopic (right) subjects. X-axis: AUCSF of the tested eye when the untested eye was covered with a translucent medium; Y-axis: AUCSF of the tested eye when the untested eye was covered with an opaque medium. The diagonal line is the identity line with a slope of 1.0. AE: amblyopic eye; FE: fellow eye; RE: right eye; Corrected AE/LE: Amblyopic/left eye tested with glasses; Corrected FE/RE: fellow/right eye tested with glasses; Corrected AE/LE (filled diamonds): Amblyopic/left eye tested with glasses; Corrected FE/RE (open diamonds): fellow/right eye tested with glasses; Naked AE/LE (filled stars): Amblyopic/left eye tested without glasses; Naked FE/RE (open stars): fellow/right eye tested without glasses.

FIG. 9 is a table providing the power of single metrics and the best discriminator(s) in identifying amblyopia.

FIG. 10 is a table providing characteristics of myopic observers.

DETAILED DESCRIPTION

Figure 4:
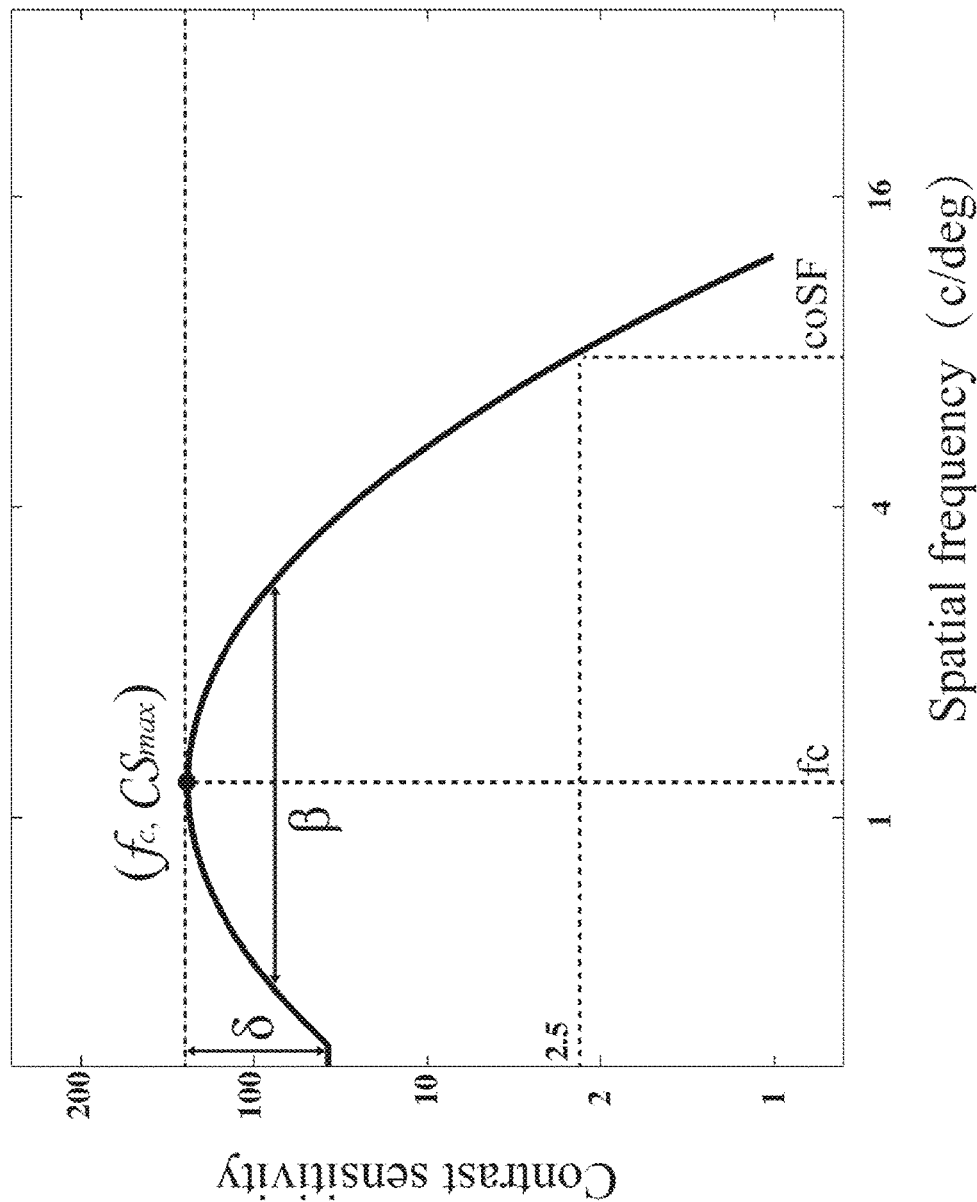
FIG. 4 is a graph CSF parameterization. The spatial contrast sensitivity function, which describes reciprocal contrast threshold as a function of spatial frequency, can be described by four parameters: (1) the peak gain, $CS_{max}$, (2) the peak frequency, $f_c$, (3) the bandwidth (full width at half-maximum), $\beta$, and (4) the truncated fall-off on the low-frequency side, $\delta$. Bayesian adaptive methods for measuring contrast sensitivity functions, of which the quick CSF method is the most prominent example, rapidly estimate the CSF by directly estimating the parameters of the CSF. Parameterizations can differ between methods but the estimation of contrast sensitivities at different spatial frequencies is the same.

Before any implementations of the invention are explained in detail, it is to be understood that the invention is not limited in its application to the details of construction and the arrangement of components set forth in the following description or illustrated in the following drawings. The invention is capable of other implementations and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. The term "set" is used broadly to refer to one or more. Also, electronic communications and notifications may be performed using other known means including direct connections, wireless connections, etc.

It should also be noted that a plurality of hardware and software based devices, as well as a plurality of different structural components may be utilized to implement the invention. Furthermore, and as described in subsequent paragraphs, the specific configurations illustrated in the drawings are intended to exemplify implementations of the invention. Alternative configurations are possible.

Amblyopia screening during childhood can be critical for early detection and successful treatment. In one embodiment, the inventors developed and evaluated a screening method that exploits the imbalanced interocular inhibition between amblyopic and fellow eyes. The inventors, during one round of testing, tested nineteen subjects with anisometropic amblyopia and twenty-two age-matched subjects with myopia. The implementation measured the area under the contrast sensitivity functions (AUCSFs) in eight monocular conditions defined by a tested eye (left, right), patching condition of the untested eye (translucent, opaque) (FIG. 1), and determined refractive status (corrected, uncorrected). For each tested eye, the analysis defined the inhibition index as the ratio between AUCSF values obtained in the translucent and opaque patching conditions of the untested eye. To evaluate the screening potential of the inhibition index, one implementation compared results from patients with amblyopia and myopia. With and without optical correction, the index was significantly lower in the amblyopic eye than in the fellow eye of the amblyopic subjects and both eyes of the myopic subjects. No significant difference was found among the two eyes of the myopic subjects and the fellow eyes of the amblyopic subjects. With the inhibition index as the predictor, a logistic regression model successfully discriminated amblyopic eyes from myopic eyes with at least near 100% accuracy in the uncorrected condition. In the corrected condition, with the inhibition index and interocular visual acuity difference as predictors, amblyopic eyes were likewise discriminated from myopic eyes with at least near 100% accuracy. This pattern of contrast sensitivity function (CSF) changes, caused by the different patching modes of the untested eye, provides a potential CSF signature to discriminate anisometropic amblyopia from myopia.

Accordingly, in at least one embodiment, manipulating the luminance level in a fellow eye drastically changed the CSF in an amblyopic eye of a patient. As used herein, an opaque patch or opaque block includes an opaque medium that does not substantially transmit light (ideally no light) to the eye. The opaque medium attenuates 90% to 100% of light, or 95% to 100% light, or 99% to 100% light. A translucent patch or translucent block includes a translucent medium that does allow light to reach the eye but blocks pattern vision. In one construction, the light through the translucent medium should have a substantially same luminance (ideally the same luminance) as without the patch but substantially zero (ideally zero) contrast. The same manipulation had no significant effect on the CSF of the fellow eye in amblyopic vision, nor on the CSF of the myopic eyes. AUCSF improved in a pinhole condition only for subjects with myopia but not for those with amblyopia. These two effects provide complementary methods, which may or may not be used together, to discriminate amblyopia from myopia. A detailed study for one embodiment of the invention will be discussed next.

1.1 Subjects

Nineteen adult subjects (mean age: 22.6±0.7 years) with anisometropic amblyopia and twenty-two myopic adults (mean age: 23.1±0.8 years) participated in the study. Detailed characteristics of the subjects, including age, sex, optical correction, and their corrected and uncorrected acuity, are listed in Tables 1 and 2 (FIGS. 2 and 3, respectively). The myopic subjects were recruited from the Institute of Psychology, Chinese Academy of Sciences, and nearby universities; the amblyopic subjects were referred from local ophthalmology/optometry clinics. All myopic subjects and the fellow eyes of the amblyopic subjects had corrected-to-normal vision. All participants were naive to psychophysical experiments. Written informed consent was obtained from each subject and their guardians/parents after explanation of the nature of the study. The protocol was approved by the IRB of the Institute of Psychology, Chinese Academy of Sciences, and carried out in accordance with the Declaration of Helsinki.

1.2 Implementation

Recently, the quick CSF method (may also be referred to as qCSF) was developed to accurately estimate the contrast sensitivity function with greatly reduced testing times. As shown in FIG. 4, the CSF is characterized by a four-parameter truncated log parabola with four parameters: (1) the peak gain ($CS_{max}$); (2) the peak spatial frequency ($f_c$); (3) the truncated fall-off on the low-frequency side ($\delta$); and (4) the bandwidth (full width at half-maximum) ($\beta$). Different combinations of parameter values are assigned an initial probability, creating a four-dimensional probability density function (PDF). The PDF is updated using Bayes' rule based on subject's response in detecting grating or other optotypes of a certain combination of spatial frequency and contrast level. The spatial frequency and contrast of the stimulus in the next trial is chosen from all possible combinations of spatial frequency and contrast conditions such that the expected outcome will result in the largest reduction in the entropy (i.e. largest information gain) of the PDF. The method has been recently validated in applications studying amblyopia, peripheral vision, and second-order perception.

The implemented quick CSF procedure can be done as described in U.S. Pat. No. 7,938,538, issued on May 10, 2011, the entire content of which is incorporated herein by reference. Another possible procedure for rapid measurement of visual sensitivity is disclosed in PCT Publication No. WO 2013/170091, published on Nov. 14, 2013, the entire content of which is incorporated herein by reference.

One exemplary system utilizing the invention, including performing the quick CSF procedure and identifying an eye disorder of an observer, is shown in FIG. 5 as system 100. The system 100 includes a display 110 coupled to a user interface 120 and a computing system 130. An observer (or subject, user, or patient) 140 can interact with the user interface 120 and/or display 110. The system can include, for example, a personal computer or a mobile device such as a smart phone or tablet computer and can have network connectivity for communication with other computing systems or servers. The user interface 120 can be integrated with the display 110, for example, as a touch screen display. High quality visual stimuli, with accurate control of luminance/color, spatial pattern and layout, and display timing can be accommodated based on display resolution and size. A constant viewing distance may be achieved through the use of a chinrest or other similar devices. The observer 120 can perform the quick CSF procedure using the system by, for example, viewing indicia (e.g., gratings, letters, numbers) on the display 110, as discussed in U.S. Pat. No. 7,938,538 or PCT Publication No. WO 2013/170091. In one implementation, the observer provides response to the interface 120, while the computing system 130 establishes the quick CSF. The observer 140 can indicate or draw a response using the user interface 120. Identification can be done by key press of recognized letters, and/or the observer can verbally respond for recognition by verbal recognition software. It is also envisioned that the observer may provide response through the assistance of a clinician proctoring the observer. The computing system 130 can determine the result of the stimulus test, determine the quick CSF, and whether the observer 120 has a visual impairment as further discussed below. An example system 100 is an IBM PC compatible computer with a keyboard, running software for stimulus presentation, in addition to scientific computing software that implements the quick CSF algorithm. The stimuli were displayed on a Dell 17-inch color cathode ray tube (CRT) monitor, whose refresh rate was set at 100 Hz. Matlab programs can be written with Psychtoolbox extensions to be used to present visual stimuli; the computer keyboard is used to collect observer responses; and the quick CSF algorithm is used to select stimulus conditions and estimate the contrast sensitivity function.

In another construction, the hardware setup for a quick CSF implementation includes a small-form factor PC (Intel i5 CPU, 4 GB RAM) and a large-format screen for stimulus display, such as a 46" diagonal with a resolution of 1920 by 1080 pixels. At a viewing distance of 400 cm, the screen allows the display of stimuli in a spatial frequency range from 1.4 to 36.2 cycles per degree, which includes the whole set of frequencies mandated by the Food and Drug Administration (FDA, 1.5 to 18 cpd). Also according to FDA standards, mean screen luminance is calibrated to 85 cd/m$^2$. All device functionality including power control can be accessed through a handheld tablet device. A near field communication (NFC) reader provides an authentication mechanism through smartcards. External interfacing for data export can be provided by an Ethernet and a USB port. The small-form factor PC can run a regular Linux operating system. However, the operating system is transparent to the user because all user interaction is performed on the tablet remote control, and the vision test software permanently runs in full screen mode. The PC-side software can be written in C++; the graphics display further uses OpenGL shaders and implements spatio-temporal dithering to increase bit depth of the screen. For convenience, the software can automatically calculate several features of the CSF: threshold sensitivities at five individual spatial frequencies mandated by the FDA; CSF acuity, the intersection of the CSF with the x-axis (i.e. spatial frequency where contrast threshold is 100%); and a summary statistic, the area under the CSF in the range from 1.5 to 18 cpd. Raw data, such as the trial history and the full posterior distribution of CSF parameters can be stored in a database and can be exported via a web-based database interface or the USB port. The tablet remote control can be an Android image that always runs the remote control app in the foreground. In one implementation, the observer reads out the letters on the screen. An examiner, who is presented with the ground truth, codes the responses as correct or incorrect; an "I don't know" response can also be coded. In order to reduce spatial uncertainty, each stimulus presentation is preceded by markers indicating the spatial position and scale of the upcoming stimulus. The examiner can repeat this marker presentation using the "Prompt" button. After response entry, the examiner can initiate the next trial; if necessary, previous responses can be undone as well. After performing the quick CSF test, the system can process the underlining data for further analysis as discussed in more detail herein.

Figure 6:
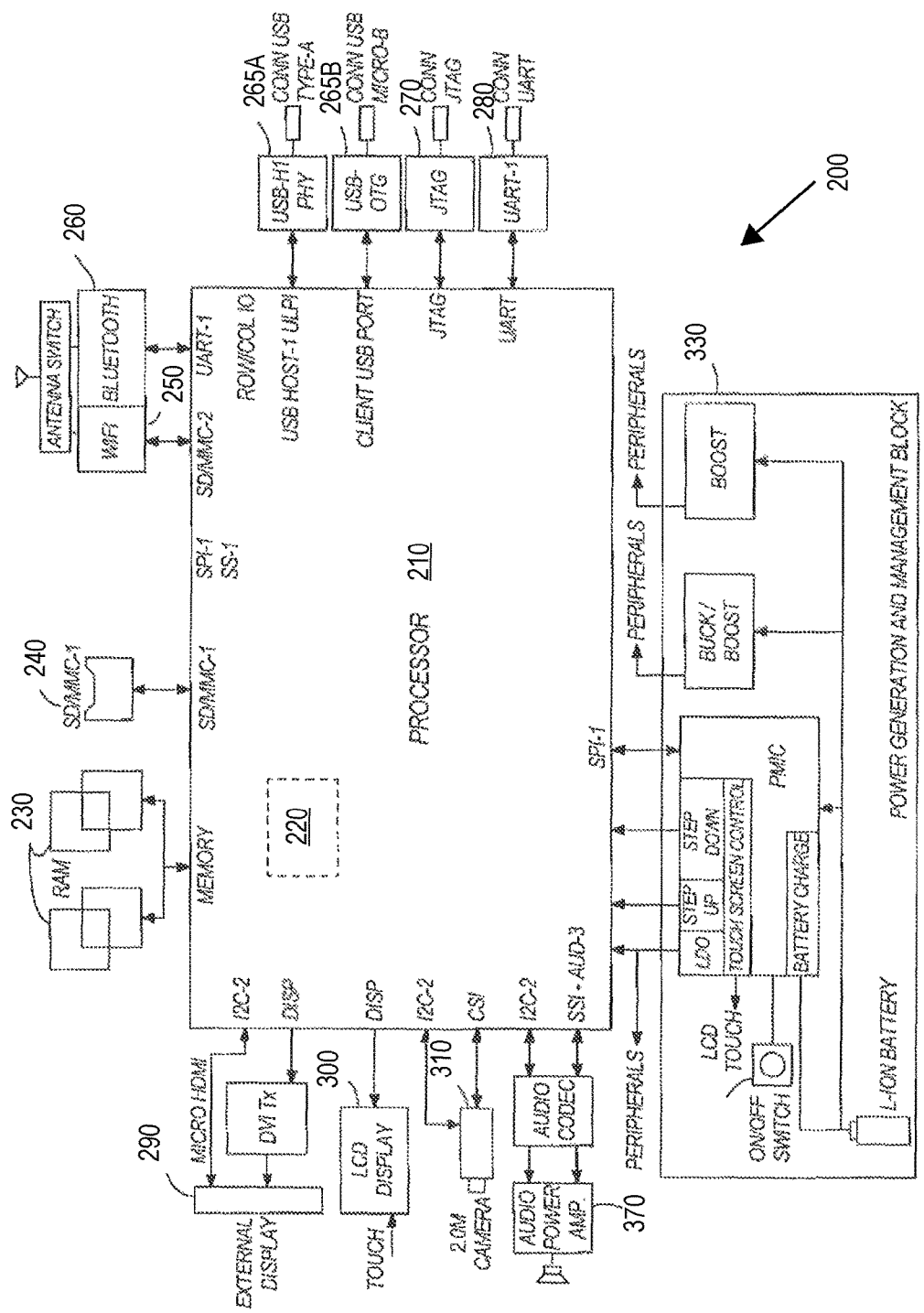
FIG. 6 is a block diagram illustrating a device for implementing the quick CSF procedure and identifying an eye disorder of an observer.

Alternatively, the system can take the form of a single device. FIG. 6 shows a block diagram of one construction of the device 200. The device 200 includes a printed circuit board ("PCB") that is populated with a plurality of electrical and electronic components that provide power, operational control, and protection to the device 200. With reference to FIG. 6, the device 200 includes a processor 210. The processor 210 is a controller for controlling the device 200. In one construction, the processor 210 is an applications processor. More specifically, the applications processor has internal instruction and data caches, multimedia capabilities, external memory interfacing, and interfacing flexibility. Of course, other processing units, such as other microprocessors, microcontrollers, digital signal processors, etc., can be used in place of the processor 210.

The device 200 includes memory, which can be internal to the processor 210 (e.g., memory 220), external to the processor 200 (e.g., RAM 230), or a combination of both. Exemplary memory includes a read-only memory ("ROM"), a random access memory ("RAM"), an electrically erasable programmable read-only memory ("EEPROM"), a flash memory, a hard disk, or another suitable magnetic, optical, physical, or electronic memory device. The processor 210 executes software that is capable of being stored in the RAM (e.g., during execution), the ROM (e.g., on a generally permanent basis), or another non-transitory computer readable medium such as another memory or a disc. The device 200 also includes input/output ("I/O") systems that include routines for transferring information between components within the processor 210 and other components of the device 200 or external to the device 200.

Software included in the implementation of the device 200 is stored in the memory 220 of the processor 210, RAM 230, ROM, or external to the device 200. The software includes, for example, firmware, one or more applications, program data, one or more program modules, and other executable instructions. The processor 210 is configured to retrieve from memory and execute, among other things, instructions related to the control processes and methods described below for the device 200. For example, the processor 210 is configured to execute instructions retrieved from the memory 220, RAM 230, and/or ROM for providing an adaptive PR procedure.

One memory shown in FIG. 6 is RAM 230, which can be a double data rate (DDR2) synchronous dynamic random access memory (SDRAM) for storing data relating to and captured during the operation of the device 200. In addition, a secure digital (SD) or multimedia card (MMC) can be coupled to the device 200 for transferring data from the device 200 to the memory card via slot 240. Of course, other types of data storage devices can be used in place of the data storage devices shown in FIG. 6.

The device 200 can also include multiple bi-directional radio communication capabilities. Specific wireless portions that can be included with the device 200 are a WiFi bi-direction radio communication portion 250 and a Bluetooth bi-direction radio communication portion 260. The WiFi portion 250 and Bluetooth portion 260 include a WiFi communication interface, a Bluetooth communication interface, an antenna switch, and a related antenna, all of which allows wireless communication following the WiFi Alliance standard and Bluetooth Special Interest Group standard. Of course, other wired, wireless local area network (WLAN) standards, and wireless personal area networks (WPAN) standards can be used with the device 200.

The device 200 can include multiple communication portions for wired communication. Exemplary circuitry and ports for receiving a wired connector include a portion and related port for supporting universal serial bus (USB) connectivity 265, including a Type-A port and a Micro-B port; a portion and related port for supporting Joint Test Action Group (JTAG) connectivity 270, and a portion and related port for supporting universal asynchronous receiver/transmitter (UART) connectivity 280. Of course, other wired communication standards and connectivity can be used with or in place of the types shown in FIG. 6.

Another device connectable to the device 200, and therefore supported by the device 200, is an external display. The connection to the external display can be made via a micro High-Definition Multimedia Interface (HDMI) 290, which provides a compact audio/video interface for transmitting uncompressed digital data to the external display. The use of the HDMI connection 290 allows the device 200 to transmit video (and audio) communication to an external display. Of course other connection schemes, such as DVI, can be used with the device 200.

The device 200 includes a touch screen I/O device 300 for providing a user interface with the observer. The touch screen display 300 can be a liquid crystal display (LCD) having a resistive, capacitive, or similar touch-screen technology. It is envisioned that multitouch capabilities can be used with the touch screen display 300 depending on the type of technology used. Alternative means for providing input to the device 200 are envisioned, including wired and wireless input devices.

The device 200 includes a camera 310 allowing the device to take pictures or video. The resulting image files can be used to document a procedure or an aspect of the procedure, such as viewing distance. Similarly, the device 200 includes an audio portion 370 having an audio codec circuit, audio power amplifier, and related speaker for providing audio communication to the observer, such as the clinician or the patient.

The device 200 further includes a power generation and management block 330. The power block 330 has a power source (e.g., a lithium-ion battery) and a power supply for providing multiple power voltages to the processor, LCD touch screen, and peripherals.

The device 200 can be a handheld computing tablet with touch screen capabilities. The tablet is a portable personal computer with a touch screen, which is typically the primary input device. However, an external keyboard or mouse can be attached to the device 200. The tablet allows for mobile functionality not associated with even typical laptop personal computers, which can be used in some embodiments of the invention. It is also envisioned that the device 200 can be coupled with a remote server that implements aspects of the invention discussed herein. For example, various processes discussed herein may be performed interactively between the device 200 and the remote server and/or certain processes, such as calculating areas under CSF, determining inhibition indices or optical factors, and identifying eye disorders, can be performed at a later time after the procedure at the remote server.

Briefly, with respect to the quick CSF procedure, the stimulus space consist of gratings with contrasts ranging from 0.1% to 99% in steps of 1.5 dBs and spatial frequencies ranging from 0.5 to 16 cycles per degree (cpd) in steps of 3 dBs. The quick CSF's parameter space is a four-dimensional grid; the ranges of possible CSF parameters were: 1.2 to 200 for peak gain, 0.25 to 24 cpd for peak frequency, 0.25 to 8 octaves for bandwidth, and 0.01 to 4 for truncation level. A diffused prior was used to initiate the procedure.

The CSF curve was obtained after 50 qCSF trials. The area under contrast sensitivity function (AUCSF) was calculated by integrating over spatial frequency from 0.5 to 16 cpd. The cutoff spatial frequency (coSF), defined as the spatial frequency that corresponds to a contrast sensitivity of 2.5, was computed from the CSF curve.

1.3 Stimuli

The stimuli were 2.5°×2.5° vertical sine wave gratings. To minimize edge effects, a half-Gaussian ramp ($\sigma=0.25°$) was added to the edges of the gratings to blend them into the background. Stimuli were generated using a computer running Matlab based on Psychtoolbox extensions and presented on a gamma-corrected monitor with a spatial resolution of 1600×1200 pixels and a refresh rate of 85 Hz. A circuit was used to produce 14-bit gray-level resolution. The mean luminance of the display was 28.3 cd/m$^2$. A chin rest was used to constrain head movements during the experiment. Subjects viewed the displays in fovea in a dimly light room at a distance of 1.14 m.

1.4 Procedure

A two-interval forced choice (2IFC) paradigm was used in the qCSF procedure. Each trial consisted of an initial 294-ms fixation in the center of the display and two 153-ms stimulus intervals separated by an inter-stimulus interval (ISI) of 588-ms. A brief tone signaled the onset of each interval. The grating was only presented in one of the two intervals. Subjects were asked to indicate the interval that contained the grating using the computer keyboard. Further discussion regarding the quick CSF procedure, including how to accomplish multiple trials, can be found in U.S. Pat. No. 7,938,538 and PCT Publication No. WO 2013/170091.

1.5 Design

Visual acuity (VA) was measured for both eyes under optically corrected and uncorrected conditions using a Chinese Tumbling E chart with the untested eye covered by an opaque patch. To minimize effects of optical adaptation, visual acuity in the naked eye condition was measured at least 30 minutes after subjects took off their glasses.

The CSF was measured in eight test conditions: 2 tested eyes (left/right eyes for myopic subjects or amblyopic/ fellow eyes for amblyopic subjects)×2 levels of optical correction (with/without glasses)×2 patching conditions (the untested eye covered with opaque or translucent medium). While the opaque patch blocked light completely, the translucent patch deprived form perception and lowered stimulus luminance by about 20%, i.e., the mean luminance in the non-tested eye was about 80% of that of the tested eye or 22.6 cd/m².

Because the study was interested in interocular inhibition index, subjects who did not complete tests in both patching conditions, mainly due to scheduling difficulties, were excluded from statistical analysis. We ended up with 19 effective measurements in the amblyopic eye with glasses condition, 7 in the amblyopic eye without glasses condition, 19 in the fellow eye with glasses condition, 6 in the fellow eye without glasses condition, 40 in the myopic eye with glasses condition (20 left and 20 right eyes), and 21 in the myopic eye without glasses condition (11 left and 10 right eyes). To guarantee that CSFs were measured at the same light adaption level, we asked subjects to step out of the test room into a regular indoor light room for about five minutes between tests. The four conditions with glasses and the other four without glasses were tested in separate blocks and counterbalanced across subjects.

1.6 Analysis

Figure 7:
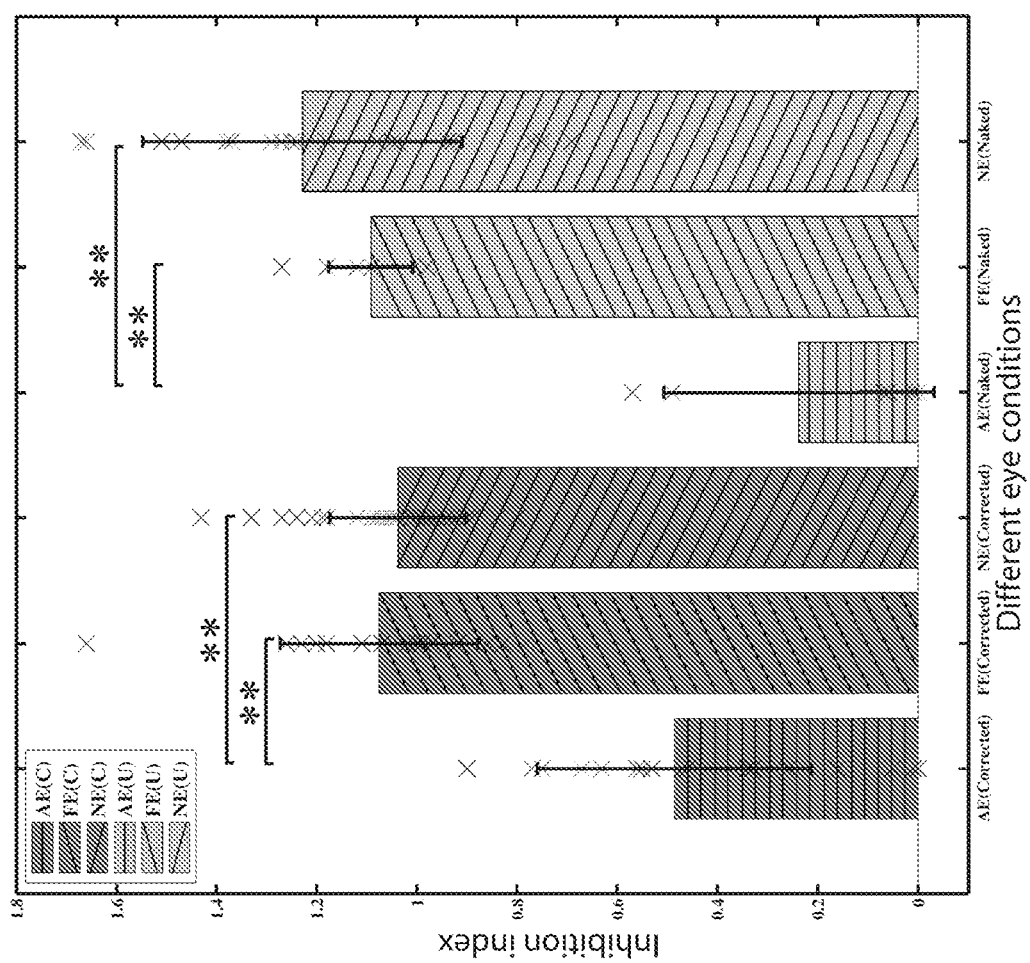
FIG. 7 is a graph representing inhibition indices in amblyopic and myopic eyes. The first three bars (dark gray) represent data from the amblyopic (horizontal line) and fellow eyes of the amblyopic subjects (left oriented line), and the average of the left and right eyes of the myopic subjects (right oriented) in the optically corrected condition. The last three bars (light gray) represent data in the naked eye condition. The crosses stand for individual data.

For each tested eye, we defined the inhibition index for that eye to be the AUCSF ratio between the translucent and opaque patching conditions (FIGS. 7 and 8, respectively). An inhibition index significantly below 1.0 signifies that the tested eye is inhibited more by a translucently patched untested eye than by an opaquely patched untested eye. An index near 1.0 signifies that the tested eye is equally inhibited by the opaquely or translucently patched untested eye.

The lower the inhibition index is, the greater the imbalance between the two eyes. Pearson's correlations between the degree of amblyopia (e.g. visual acuity and AUCSF difference between amblyopic and fellow eyes) and the inhibition indices were calculated using SPSS for Windows (Version 19.0; SPSS, Inc., Chicago, Ill., USA).

To determine the effective predictors that discriminate anisometropic amblyopia from myopia, the implementation applied a logistic regression model with amblyopia as the dichotomized outcome, and inhibition index and interocular differences in visual acuity, AUCSF, and high-cutoff spatial frequency as independent predictors (Version 19.0; SPSS, Inc., Chicago, Ill., USA):

$$P(amb) = \frac{\exp(\beta_0 + \beta_1 \cdot \text{ratio} + \beta_2 \cdot \text{area} + \beta_3 \cdot \text{VA} + \beta_4 \cdot \text{coSF})}{1 + \exp(\beta_0 + \beta_1 \cdot \text{ratio} + \beta_2 \cdot \text{area} + \beta_3 \cdot \text{VA} + \beta_4 \cdot \text{coSF})} \quad (1)$$

where P(amb) is the probability of an eye being amblyopic, ratio represents inhibition index, area represents interocular AUCSF difference, VA represents interocular visual acuity difference, coSF represents interocular cutoff spatial frequency difference, i.e., the difference between the cutoff spatial frequencies in the two eyes, and $\beta$'s are the coefficients.

A stepwise selection method was used to select effective predictors, in which the inclusion of a particular predictor is based on the significance of the score statistic, and the exclusion of a particular predictor is based on the probability of a likelihood-ratio statistic (Forward Selection-Conditional in SPSS 19.0). The logistic regression models in the corrected and uncorrected conditions were evaluated separately.

2. Results

The discussed implementation compared visual acuity in the two eyes of the amblyopic and myopic subjects, for both the optically corrected and uncorrected conditions. Under correction, there were significant differences (p<0.01) between acuities in the amblyopic (0.44±0.08, mean Log MAR±s.e.) and fellow eyes (−0.04±0.02) of the amblyopic subjects, and between acuity in the amblyopic eye and corrected-to-normal eyes of the myopic subjects (−0.04±0.02). Without optical correction, no significant visual acuity difference was found among the amblyopic, fellow, and myopic eyes (0.41±0.10, 0.29±0.10 and 0.52±0.10, respectively; p>0.10). Visual acuity was not a good metric for discriminating amblyopia from myopia without optical correction in these subjects.

From CSFs obtained in each condition, we derived the area under CSF (AUCSF) and the cutoff spatial frequencies. The AUCSF characterizes spatial vision over a wide range of spatial frequencies. The cutoff spatial frequency characterizes the spatial resolution limit of the visual system. Visual acuity and cutoff spatial frequency were highly correlated in all the test conditions (Pearson Correlation, R=−0.717, P<0.01).

Without optical correction, the AUCSF in the amblyopic eyes (8.92±2.27) was comparable to that in the fellow eyes (10.00±2.07) and myopic eyes (6.35±0.92 average across two eyes) in the opaque patching condition (p>0.10). However, the AUCSF in the amblyopic eyes (1.26±0.60) was significantly lower than that in the fellow eyes (10.71±2.88) and lower than the myopic eyes (5.40±0.92) in the translucent patching condition (p<0.01 and p<0.05, respectively). With optical correction, the AUCSF in the amblyopic eye (9.04±1.18) was significantly lower than that in the fellow eyes (15.86±0.88) and myopic eyes (16.80±0.72) in the opaque patching condition (p<0.01). In addition, the AUCSF in the amblyopic eyes (3.71±0.66) was significantly lower than that in the fellow eyes (16.71±0.82) and myopic eyes (16.79±0.72) in the translucent patching condition (p<0.01).

With optical correction, the inhibition index was significantly lower (all p<0.01) in the amblyopic eyes (0.43±0.07) than that in the fellow eyes (1.08±0.05) of the amblyopic subjects, and in both eyes of the myopic subjects (1.10±0.08 and 1.03±0.04 for left and right eyes, respectively). Removing optical correction led to the same qualitative results: the inhibition index was 0.17±0.09 for the amblyopic eyes, and 1.15±0.05, 1.17±0.09 and 1.28±0.10 for the fellow eyes of the amblyopic subjects, and the left and right eyes of the myopic subjects, respectively. No significant difference was found among the left and right eyes of the myopic subjects and the fellow eyes of the amblyopic subjects in both optical correction conditions (all p>0.10). The inhibition index was highly correlated with interocular visual acuity difference in the optically corrected condition (R=0.639, p<0.01) but not in the uncorrected condition (R=0.003, p>0.1).

The logistic regression analysis revealed that the best discriminating factor(s) was the inhibition index in the uncorrected condition, and a combination of inhibition index and the interocular visual acuity difference in the corrected condition. With the inhibition index as the predictor, amblyopic and myopic eyes were discriminated with 100% accuracy in the naked eye condition ($\beta_0$=171.27, $\beta_1$=−272.36; $\chi(1)$=20.73, p<0.01). In the optically corrected condition, using the inhibition index as the single predictor discriminated amblyopic from myopic eyes with 82.9% accuracy; adding interocular visual acuity difference as a second predictor increased the accuracy to 100% ($\beta_0$=306.82, $\beta_1$=−260.48; $\beta_4$=−12.30; $\chi(2)$=56.62, p<0.01).

The predictive powers of the variables discriminating amblyopia from myopia, including interocular visual acuity difference, interocular cutoff spatial frequency difference, interocular AUCSF difference, and inhibition index, are listed in Table 3 (FIG. 9). In the uncorrected condition, only the inhibition index successfully identified amblyopia at 100% accuracy; in the optically corrected condition, interocular visual acuity difference predicted amblyopia with 95.1% accuracy; and adding inhibition index increased the accuracy to 100%.

3. Discussion

By manipulating the patching condition (translucent vs. opaque) in the untested eye and exploiting the asymmetrical interocular inhibition between the two eyes in amblyopia, the inventors demonstrated that the qCSF procedure in combination with patching can be used to effectively screen anisometropic amblyopia without optical correction. The results are related to interocular suppression and/or dichoptic masking from the luminance of the stimulus presented to the non-tested eye.

Most amblyopes are of anisometropic and strabismic types. In the current study, the inventors tested the efficacy of the interocular inhibition procedure to discriminate aisometropic amblyopia from myopia. Although a prior author concluded that interocular suppression and binocular combination are essentially intact in strabismic amblyopia based on results from interocular masking tests, stronger inhibition from the fellow fixating eye to the amblyopic eye has been long established as a mechanism for visual deficits in strabismic amblyopia. Application of bicuculline (a gamma-Aminobutyric acid or GABA receptor blocker) has been found to be effective in reversing the binocular responsiveness of cortical cells in strabismic animals, suggesting that the input from the strabismic eye may be functionally suppressed in strabismic amblyopia. Using a global motion identification paradigm, several studies have demonstrated that interocular suppression might play a primary role in both anisometropic and strabismic amblyopia. Others have found that contrast interference threshold (the lower the threshold, the stronger the inhibition from the fellow eye to the amblyopic eye) was smaller in strabismic amblyopia than in anisometropic amblyopia, indicating interocular suppression may be even stronger in strabismic amblyopia. All these results suggest that the interocular inhibition procedure can be applied to screen strabismic amblyopia.

Early and accurate detection are two key components of amblyopia treatment. Early vision screening is strongly recommended by the American Academy of Pediatrics (AAP) to detect amblyopia to allow successful treatment. On the other hand, previous findings recommend using joint tests to screen with greater diagnostic accuracy. The test developed and evaluated in the current study can be applied without eye alignment, refractive error measurement, and prescription of eye glasses. The test is efficient, easy-to-perform, and can be quite affordable.

Recently, the qCSF procedure has been implemented on an iPad, making it possible to conduct our screening on a portable device and simultaneously on many subjects.

4. The Pinhole Procedure

A pinhole aperture permits only the central light rays to enter into the eye. The diameter of an ideal pinhole aperture is determined by the following the formula:

$$d = \sqrt{2(f_0 + f_1)\lambda_0} \quad (2)$$

where d is pinhole diameter, $f_0$ is the focal length of human eye, $f_1$ is the distance from pinhole aperture to the cornea, and $\lambda_0$ is the light wavelength. In typical settings, $f_0$=22-24 mm, $f_1$=5 to 10 mm, $\lambda_0$=740 nm. The diameter of an ideal pinhole aperture thus ranges from 0.2 to 0.22 mm. The light rays are less likely disrupted by refractive errors such as myopia, hyperopia and astigmatism.

For visual impairments caused by neurologic disorders, such as optic neuritis or amblyopia, vision will not improve with a pinhole aperture. For certain visual impairments, such as opacities in the media (e.g., cataract), vision may even get worse with a pinhole aperture. Visual examination with a pinhole aperture has been used as a first-hand quick, simple, yet accurate, method of determining whether a patient's impaired vision is due to a refractive error or other pathologies in clinical practice.

Previous applications of the pinhole aperture test have focused on its potential effects on visual letter acuity. Since visual acuity is only an assay of the quality of vision in high luminance and high contrast conditions, we aimed to evaluate the effects of a pinhole aperture on contrast sensitivity function (CSF), a more comprehensive measure of spatial vision.

4. 1. Methods 4. 1.1 Subjects

Three myopic adults (mean age: 28.7±3.7 years) participated in the study. Detailed characteristics of the subjects, including age, sex, optical correction, and their corrected and uncorrected acuity, are listed in Table 4 (FIG. 10). The myopic subjects were recruited from the Institute of Psychology, Chinese Academy of Sciences. All myopic subjects had corrected-to-normal vision and were naive to psychophysical experiments. Written informed consent was obtained from each subject after explanation of the nature of the study. The experimental protocol was approved by the Institutional Review Board of the Institute of Psychology, Chinese Academy of Sciences, and carried out in accordance with the Declaration of Helsinki.

4.1.2 Stimuli and Apparatus

Figure 11:
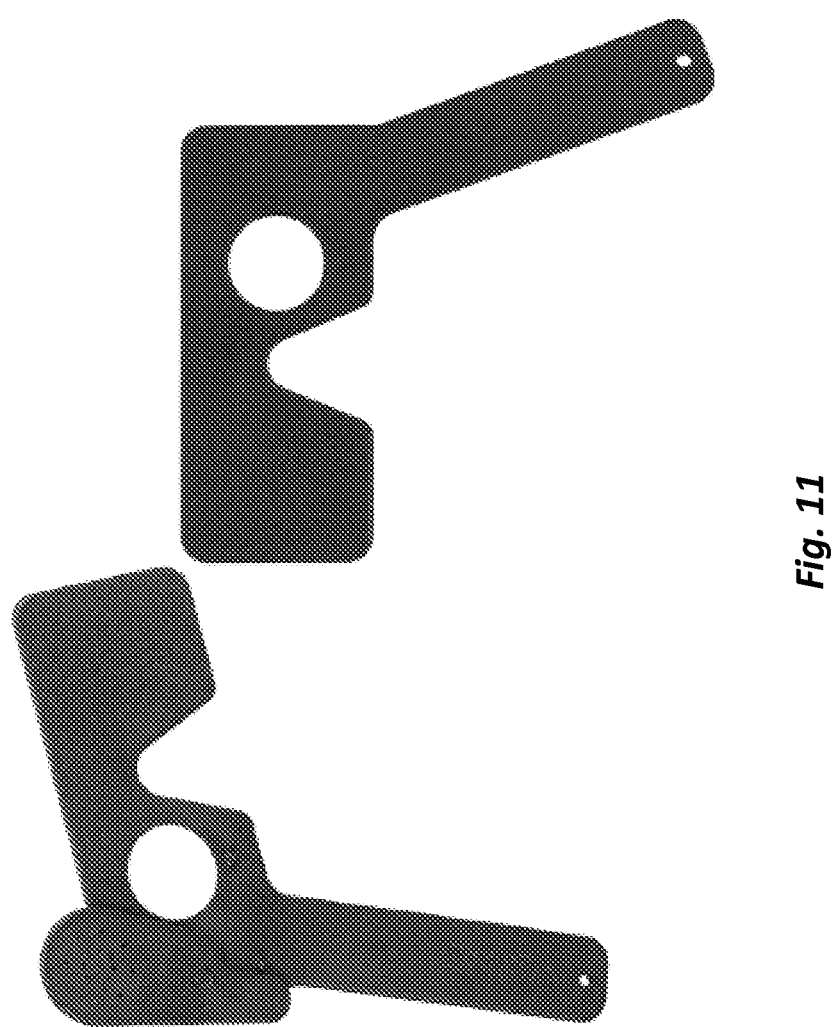
FIG. 11 is an illustration of a pinhole aperture.

The stimuli were 2.5°×2.5° vertical sine wave gratings. To minimize edge effects, a half-Gaussian ramp (σ=0.25°) was added to the edges of the gratings to blend them into the background. They were generated using a computer running Matlab based on Psychtoolbox extensions and presented on a gamma-corrected monitor with a spatial resolution of 1600×1200 pixels and a refresh rate of 85 Hz. A circuit was used to produce 14-bit gray-level resolution. The mean luminance of the display was 31.3 cd/m². The luminance of the display through a 10% density neutral density (ND) filter and a 2 mm diameter pinhole aperture were 2.7 cd/m² and 3.1 cd/m², respectively (FIG. 11). A chin rest was used to constrain head movements during the experiment. Subjects viewed the displays in fovea in a dimly lighted room at a distance of 1.14 m.

4.1.3 Procedure and Analysis

A two-interval forced choice (2IFC) paradigm was used in the quick CSF procedure. Each trial consisted of an initial 294-ms fixation in the center of the display and two 153-ms stimulus intervals separated by an inter-stimulus interval (ISI) of 588-ms. A brief tone signaled the onset of each interval. The grating was only presented in one of the two intervals. Subjects were asked to indicate the interval that contained the grating using the computer keyboard. No feedback was provided.

4.1.4 Design

For a given eye, we measured CSF in the naked eye (without glasses) with the pinhole aperture and the ND filter, and optically corrected eye (with glasses) with the ND filter. Three sets of CSFs were measured in five eyes.

4.1.5 Analysis

For each CSF, we computed the Area Under CSF (AUCSF) and cutoff spatial frequency that corresponds to a contrast threshold of 0.5, and compared across three testing conditions using SPSS for Windows (Version 19.0; SPSS, Inc., Chicago, Ill., USA).

4.2 Results

Seen through a pinhole aperture in the naked (uncorrected) eye, significantly improved AUCSF (from 2.65±2.18 to 8.88±2.06, p<0.05) and cutoff spatial frequency (3.25±1.9 to 9.17±2.12 cpd; p<0.05). Since the diameter of the pinhole aperture we used in the current experiment was 2 mm and there was some residual distance between the pinhole aperture and the pupil, light scattering may still play a role in our experimental setting. As a result, wearing corrective glasses can further improve AUCSF to 19.21 (±1.96) and cutoff spatial frequency to 17.79 (±2.12) cpd (both p<0.01). A setup based on a better pinhole aperture and/or retina illumination methods (e.g., Maxwellian View) would greatly reduce light scattering through the pinhole aperture and improve AUCSF.

We computed the optical factor, that is, the ratio of AUCSF in the uncovered naked eye condition over that in the pinhole naked eye condition. The average optical factor is 3.35±1.34, suggesting that the pinhole aperture significantly improved the CSF in myopic eyes.

4.3 Summary

The inventors found that for patients with myopia, AUCSF improved in the pinhole condition. For patients with amblyopia, AUCSF would not significantly change in the two conditions. The effect provides a complementary method to discriminate amblyopia from myopia/hyperopia.

Figure 12:
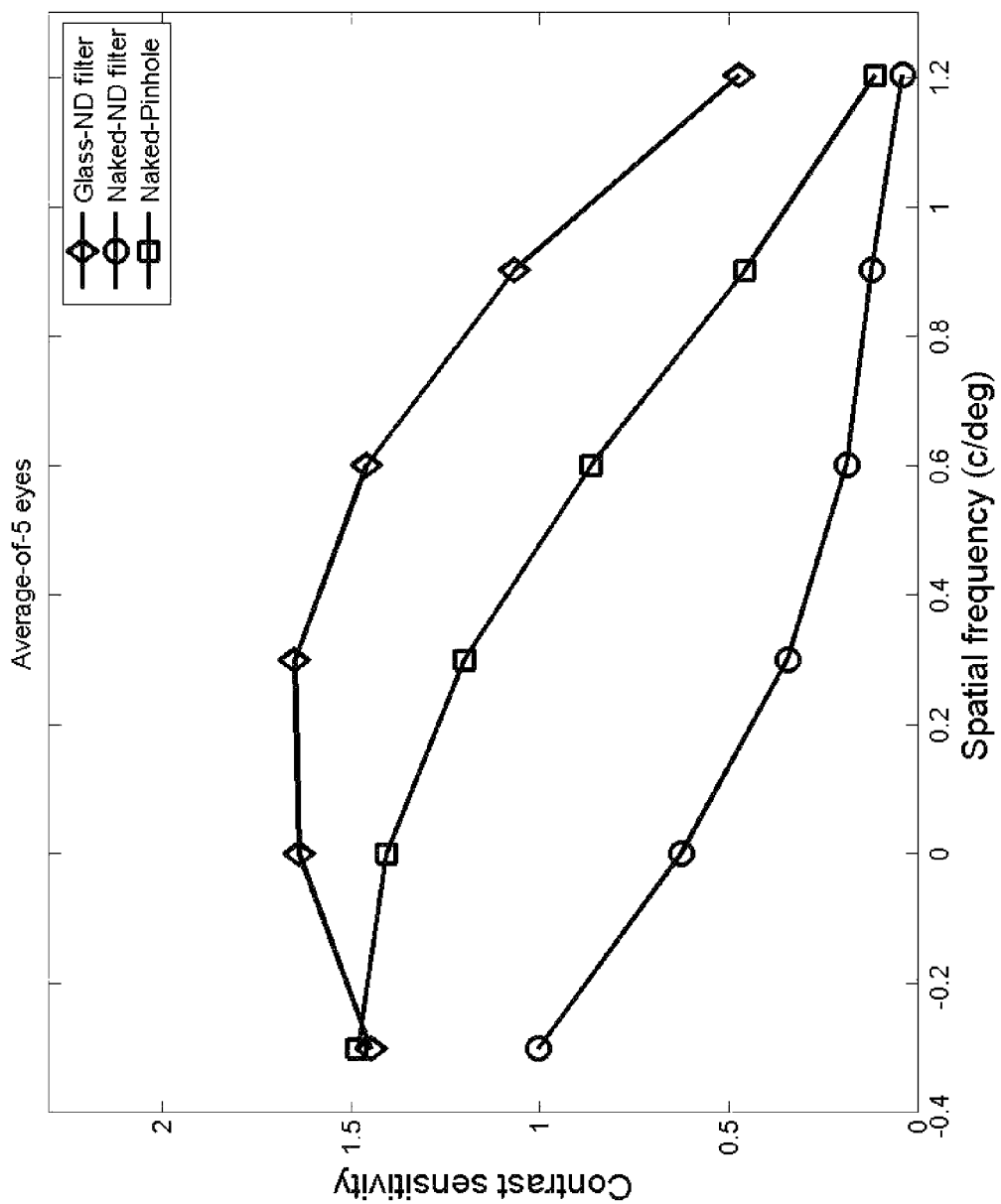
FIG. 12 shows the average CSF in the three testing conditions. Diamonds: corrected eye with the neutral density (ND) filter; Squares: Naked eye with a pinhole; Open circles: Naked eye with the ND filter.

For the pinhole version of the test, in at least one procedure, AUCSF improved in the pinhole condition for myopic eyes (see data from three myopic subjects in FIG. 12). For patients with amblyopia, AUCSF would not significantly change in the two conditions. This effect provides a complementary method to discriminate amblyopia from myopia.

For a myopic eye, a well-designed pinhole aperture can be used to eliminate effects of defective optics and generate a normal CSF, but a pinhole aperture can't improve the CSF of an amblyopic eye to normal. A comparison of CSFs collected through a pinhole aperture with CSFs of subjects with normal vision can be used to distinguish amblyopic vision from myopic/hyperopic vision.

The invention provides at least four different CSF measurements: (1) when the untested eye is patched with an opaque medium, (2) when the untested eye is patched with a translucent medium, (3) through a pinhole aperture without optical correction; (4) through a neutral density filter without optical correction. Comparison of CSFs in different conditions can be used to identify amblyopia.

An inhibition index is computed as the ratio of the AUCSF when the untested eye is covered with a translucent medium over that when the untested eye is covered with an opaque medium, or alternatively as $10^D$, where D is the difference between the AULCSF when the untested eye is covered with a translucent medium over that when the untested eye is covered with an opaque medium. An eye with an inhibition index that is significantly less than 1.0 is deemed to be or highly likely to be amblyopic, with the criterion defined by the statistical properties of the populations with and without clinically designated amblyopia. An alternative is to develop or apply statistical or machine learning procedures (e.g., discriminant analysis, logistic regression, pattern classification) to identify the best predictors and the criterion to identify an eye disorder (e.g., amblyopia) based on the distribution of the inhibition index and/or other features of the CSFs of populations with and without the eye disorder.

An optical factor is computed as the ratio of the AUCSF when the tested naked eye is uncovered over that when the tested naked eye sees test stimuli through a pinhole aperture, or alternatively as $10^D$, where D is the difference between the AULCSF when the tested naked eye is uncovered over that when the tested naked eye sees test stimuli through a pinhole aperture. An eye with an optical factor that is not significantly different from 1.0 is deemed to be or highly likely to be amblyopic, with the criterion defined by the statistical properties of the populations with and without clinically designated amblyopia. An alternative is to develop or apply statistical or machine learning procedures (e.g., discriminant analysis, logistic regression, pattern classification) to identify the best predictors and the criterion to identify an eye disorder (e.g., amblyopia) based on the distribution of the inhibition index and/or other features of the CSFs of populations with and without the eye disorder.

Thus, the invention provides, among other things, a new and useful method and apparatus for identifying an eye disorder of an observer. Various features and advantages of the invention are set forth in the following claims.

What is claimed is:

1. A method of identifying an eye disorder of an observer, the method being accomplished with an apparatus comprising a display, a user interface, and a processor, the method comprising:
   the display generating first stimuli for the observer while an untested eye of the observer is covered with a translucent medium, the first stimuli being generated as part of a first trial for a tested eye of the observer;
   the display generating second stimuli for the observer while the untested eye of the observer is covered with an at least substantially opaque medium, the second stimuli being generated as part of a second trial for the tested eye;
   the user interface receiving first input for the first trial;
   the user interface receiving second input for the second trial;
   the processor determining a first contrast sensitivity function (CSF) using the first input;
   the processor determining a second contrast sensitivity function (CSF) using the second input;
   the processor calculating a first area under contrast sensitivity function (AUCSF) for the first CSF;
   the processor calculating a second area under contrast sensitivity function (AUCSF) for the second CSF;
   the processor defining an inhibition index for the first and second trials as the ratio of the first AUCSF over the second AUCSF or as the ratio of the second AUCSF over the first AUCSF;
   the processor identifying an eye disorder for the tested eye of the observer using the inhibition index.

2. The method of claim 1, wherein the display generating first stimuli for the observer includes the display generating a series of indicia with differing spatial frequencies, contrasts, or spatial frequencies and contrasts to the observer.

3. The method of claim 2, wherein the indicia are selected from the group consisting of letters and gratings.

4. The method of claim 1, and further comprising the processor performing a first quick contrast sensitivity function procedure for the first trial, wherein the display generating the first stimuli and the user interface receiving the first input occurs while performing the first quick contrast sensitivity function procedure.

5. The method of claim 4, wherein the first CSF is a first quick CSF.

6. The method of claim 4, and further comprising the processor performing a second quick contrast sensitivity function procedure for the second trial, wherein the display generating the second stimuli and the user interface receiving the second input occurs while performing the second quick contrast sensitivity function procedure.

7. The method of claim 1, wherein the processor calculates the first AUCSF by integrating the first CSF over spatial frequencies from a first spatial frequency to a second spatial frequency.

8. The method of claim 1, wherein the processor identifying the eye disorder includes identifying whether the observer has amblyopia based on the inhibition index.

9. The method of claim 1, and further comprising displaying an output to the observer with a result of whether the observer has an eye disorder.

10. The method claim 1, and further comprising
the display generating third stimuli for the observer while an untested eye of the observer is covered with an at least substantially opaque medium and a tested eye of the observer is substantially uncovered, the third stimuli being generated as part of a third trial for the tested eye of the observer;
the display generating fourth stimuli for the observer while the untested eye of the observer is covered with the at least substantially opaque medium and the tested eye views the display through a pinhole aperture, the fourth stimuli being generated as part of a fourth trial for the tested eye;
the user interface receiving third input for the third trial;
the user interface receiving fourth input for the fourth trial;
the processor determining a third contrast sensitivity function (CSF) using the third input;
the processor determining a fourth contrast sensitivity function (CSF) using the fourth input;
the processor calculating a third area under contrast sensitivity function (AUCSF) for the third CSF;
the processor calculating a fourth area under contrast sensitivity function (AUCSF) for the fourth CSF;
the processor defining an optical factor for the third and fourth trials as the ratio of the third AUCSF over the fourth AUCSF or as the ratio of the fourth AUCSF over the third AUCSF;
the processor further identifying the eye disorder for the tested eye of the observer using the optical factor.

11. The method of claim 10, wherein the processor identifying the eye disorder includes identifying whether the observer has amblyopia based on the inhibition index, and identifying whether the observer has amblyopia or at least one selected from a group consisting of myopia and hyperopia based on the optical factor.

12. A method of identifying an eye disorder of an observer, the method being accomplished with an apparatus comprising a display, a user interface, and a processor, the method comprising:
the display generating first stimuli for the observer while an untested eye of the observer is covered with an at least substantially opaque medium and a tested eye of the observer is substantially uncovered, the first stimuli being generated as part of a first trial for the tested eye of the observer;
the display generating second stimuli for the observer while the untested eye of the observer is covered with the at least substantially opaque medium and the tested eye views the display through a pinhole aperture, the second stimuli being generated as part of a second trial for the tested eye;
the user interface receiving first input during the first trial;
the user interface receiving second input for the second trial;
the processor determining a first contrast sensitivity function (CSF) using the first input;
the processor determining a second contrast sensitivity function (CSF) using the second input;
the processor calculating a first area under contrast sensitivity function (AUCSF) for the first CSF;
the processor calculating a second area under contrast sensitivity function (AUCSF) for the second CSF;
the processor defining an optical factor for the first and second trials as the ratio of the first AUCSF over the second AUCSF or as the ratio of the second AUCSF over the first AUCSF;
the processor identifying an eye disorder for the tested eye of the observer using the optical factor.

13. The method of claim 12, wherein the display generating first stimuli for the observer includes the display generating a series of indicia with differing spatial frequencies, contrasts, or spatial frequencies and contrasts to the observer.

14. The method of claim 3, wherein the indicia are selected from the group consisting of letters and gratings.

15. The method of claim 12, and further comprising the processor performing a first quick contrast sensitivity function procedure for the first trial, wherein the display generating the first stimuli and the user interface receiving the first input occurs while performing the first quick contrast sensitivity function procedure.

16. The method of claim 15, wherein the first CSF is a first quick CSF.

17. The method of claim 15, and further comprising the processor performing a second quick contrast sensitivity function procedure for the second trial, wherein the display generating the second stimuli and the user interface receiving the second input occurs while performing the second quick contrast sensitivity function procedure.

18. The method of claim 12, wherein the processor calculates the first AUCSF by integrating the first CSF over spatial frequencies from a first spatial frequency to a second spatial frequency.

19. The method of claim 12, wherein the processor identifying an eye disorder includes identifying whether the observer has amblyopia or one selected from a group consisting of myopia and based on the optical factor.

20. The method of claim 12, and further comprising displaying an output to the observer with a result of whether the observer has an eye disorder.

21. An apparatus for determining an eye disorder for an observer having a tested eye and an untested eye, the apparatus comprising:
a display;
a user interface
a processor; and
a non-transitory medium comprising instructions that when executed by the processor cause the processor to perform the method of claim 1.

* * * * *

UNITED STATES PATENT AND TRADEMARK OFFICE
CERTIFICATE OF CORRECTION

PATENT NO. : 10,357,151 B2  
APPLICATION NO. : 15/308422  
DATED : July 23, 2019  
INVENTOR(S) : Zhong-Lin Lu et al.

Page 1 of 1

It is certified that error appears in the above-identified patent and that said Letters Patent is hereby corrected as shown below:

In the Specification

Column 1, Line 15, please insert the following paragraph:
-- STATEMENT OF GOVERNMENT INTEREST
This invention was made with government support under grant number R01 EY021553 awarded by the National Institutes of Health. The government has certain rights in the invention. --

Signed and Sealed this  
Fourth Day of August, 2020

Andrei Iancu  
*Director of the United States Patent and Trademark Office*